United States Patent [19]  [11] 3,995,057
Hörrmann  [45] Nov. 30, 1976

[54] OPHTHALMOLOGICAL METHOD
[76] Inventor: Wilhelm Hörrmann, Klammstr. 3, D8100 Garmisch, Germany
[22] Filed: Apr. 28, 1975
[21] Appl. No.: 572,404

Related U.S. Application Data
[63] Continuation-in-part of Ser. No. 463,059, April 19, 1974, abandoned, which is a continuation-in-part of Ser. No. 343,094, March 20, 1973, abandoned, which is a continuation-in-part of Ser. No. 87,292, Nov. 5, 1970, abandoned, which is a continuation-in-part of Ser. No. 574,903, Aug. 25, 1966, abandoned.

[52] U.S. Cl. .................................................. 424/317
[51] Int. Cl.² .................................................. A61K 31/19
[58] Field of Search .................................... 424/317

[56] References Cited
OTHER PUBLICATIONS
Chemical Abstracts, vol. 35, 1383, (1941).

*Primary Examiner*—Frederick E. Waddell

[57] ABSTRACT
This invention relates to medicinal compositions suitable for use in treating diseases of the retina and processes for producing the compositions which are effective for causal therapy of ophthalmological disorders especially macular degeneration of the retina.

1 Claim, No Drawings

OPHTHALMOLOGICAL METHOD

This is a continuation-in-part application of my pending application Ser. No. 463,059 filed 04/19/74 which is a continuation-in-part application of my application Ser. No. 343,094 filed 03/20/73 which is a continuation-in-part application of my application Ser. No. 87,292 filed 11/05/70 which is a continuation-in-part application of my original application Ser. No. 574,903 filed Aug. 25, 1966, all abandoned.

DESCRIPTION

The invention relates to medicinal compositions suitable for use in treating diseases of the retina and more particularly to such compositions which are effective for the causal therapy of macular degenerations of the retina and of disturbances of the color sense. I have found that, prolonged administration of dimethylmaleic and dimethylfumaric acid and pharmaceutically acceptable salts and esters thereof to patients suffering from diseases of the retina, especially macular degeneration, brings about a clear improvement in eyesight.

Each of the compounds, dimethylmaleic acid or dimethylfumaric acid, may be used per se or preferably may be used in combination in pure form or as pharmaceutically acceptable salts and/or esters thereof as for example the sodium salts.

The compounds were tested in animal toxicity. It was shown that there is no practically toxicity at all. There is also evidence of healthy human persons who have voluntarily taken the compounds for weeks or months without any bad side effects. And there is also evidence of a patient suffering from macular degeneration who has taken the preparation without any interruptions daily since the year of 1965 until today and who is now in her 91st year of life.

Patients, so far treated with these compounds, were cases where the foregoing conventional therapy failed to stop the progress of the disease. They were nearly blind people who had lost most of their eyesight. This to be kept in mind judging the measured improvement reached in these cases:

| initials of Patients name | normal eyesight 1.0 before | | after this treatment | |
|---|---|---|---|---|
| | right eye | left eye | right eye | left eye |
| T.D. | 0.03 | 0.06 | 0.1 | 0.1 |
| A.P. | 0.04 | 0.04 | 0.1 | 0.1 |
| G.R. | 0.03 | 0.03 | 0.04 | 0.04 |
| M.S. | 0.02 | 0.02 | 0.04 | 0.04 |
| J.K. | 0.1 | 0.02 | 0.3 | 0.02 |
| R.S. | 0.05 | 0.05 | 0.15 | 0.15 |

The dosage is 0.2 – 8.0 gram of active compounds. The average dosage for adult persons is 2.0 – 4.0 gram of dimethylmaleic or dimethylfumaric acid, respectively 1.0 – 2.0 gram of dimethylmaleic and 1.0 – 2.0 gram of dimethylfumaric acid.

Method of administration is preferably the oral one.

What is said of dimethylmaleic acid is also true of dimethylmaleicanhydride as this easily transforms with water into dimethylmaleic acid.

What I claim is:

1. A method of treating macular degeneration of the retina in a patient comprising orally administering thereto 0.2 – 8.0 gms of dimethylmaleic anhydride, dimethylmaleic acid, dimethylfumaric acid or a sodium salt thereof.

\* \* \* \* \*